United States Patent [19]

Lin et al.

[11] Patent Number: 4,973,788
[45] Date of Patent: Nov. 27, 1990

[54] VINYLIDENE DIMER PROCESS

[75] Inventors: Kaung-Far Lin; Gunner E. Nelson, both of Baton Rouge; Carroll W. Lanier, Baker, all of La.

[73] Assignee: Ethyl Corporation, Richmond, Va.

[21] Appl. No.: 347,662

[22] Filed: May 5, 1989

[51] Int. Cl.[5] .............................................. C07C 2/26
[52] U.S. Cl. ..................................... 585/511; 585/512
[58] Field of Search ................................. 585/511, 512

[56] References Cited

U.S. PATENT DOCUMENTS 4,155,946 5/1979 Sato et al. ............................ 585/513
4,709,112 11/1987 Sato et al. ............................ 585/513

Primary Examiner—Curtis R. Davis
Attorney, Agent, or Firm—Joseph D. Odenweller; Edgar E. Spielman, Jr.

[57] ABSTRACT

Vinyl-olefins are converted to vinylidene olefin dimers at a selectivity of at least 85 mole percent by reacting a mixture of dry vinyl-olefin containing 0.001–0.04 moles of trialkyl aluminum per mole of initial vinyl-olefin at a temperature in the range of about 100°–140° C. for a time sufficient to convert at least 80 mole percent of the initial vinyl-olefin to a different material.

16 Claims, No Drawings

VINYLIDENE DIMER PROCESS

BACKGROUND

In the specification, olefins are referred to as:
"vinyl olefins" R—CH=CH₂,
"vinylidene olefins"

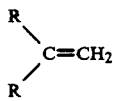

and internal olefins which are sub-divided as:
"di-substituted" R—CH=CH—R,
"tri-substituted"

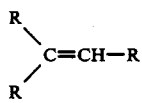

and "tetra-substituted"

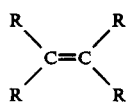

wherein R represents a hydrocarbon group. Internal olefins are also classified as "β-internal" in which the double bond is connected to the β-carbon atom as in:

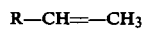

and "deep internal" which is a di-substituted olefin in which the double bond is further towards the center of the olefin as in:

wherein R' is an aliphatic hydrocarbon group containing two or more carbon atoms.

The "β-internal" olefins referred to herein are monomeric. This means they contain the same number of carbon atoms as the initial vinyl-olefins but the olefinic double bond has moved toward the center of the molecule.

The "deep internal" olefins referred to herein are dimers of the initial vinyl olefins. For example, a deep internal dimer of 1-octene contains 16 carbon atoms. They differ from vinylidene dimers in that their olefinic double bond is in the linear chain near the center of the molecule.

Vinyl-olefins can be dimerized to form deep internal olefin dimers using a catalyst such as a Friedel Craft catalyst (e.g. BF₃) The present invention is not concerned with such Friedel Craft catalyzed dimerizations.

Vinyl-olefins can also be dimerized to form vinylidene olefins as described in Ziegler U.S. Pat. No. 2,695,327. Aluminum alkyl dimerization also forms a much smaller amount of a non-vinylidene dimer referred to herein as "deep internal dimers."

Vinylidene olefins are very useful. For example they may be further dimerized using a Friedel Crafts catalyst to form a valuable synthetic lubricant as described in Shubkin U.S. Pat. No. 4,172,855.

SUMMARY

According to the present invention, vinyl olefins containing about 4–20 carbon atoms can be dimerized to selectively form vinylidene olefin dimers with very little co-production of deep internal olefin dimers and little isomerization of the initial α-olefin monomer to form internal olefin monomers, by conducting the dimerization using a very low concentration of aluminum alkyl catalyst and within a narrow, relatively low temperature range. When operating in this manner it has been possible to achieve high conversions showing at least 85 mole percent selectivity of converted vinyl-olefin to vinylidene olefin dimers.

DESCRIPTION OF THE PREFERRED EMBODIMENTS

A preferred embodiment of the invention is a process for dimerizing a vinyl-olefin monomer at a selectivity of at least 85 mole percent to vinylidene olefins, said process comprises dimerizing a vinyl-olefin containing 4 to about 30 carbon atoms in the presence of 0.001–0.04 moles of tri-alkyl aluminum catalyst per mole of said vinyl-olefin at a temperature in the range of about 100°–140° C. for a time sufficient to convert at least 80 mole percent of the initial vinyl-olefin to a different product.

Vinyl-olefins that can be used in the process include both straight and branched chain terminally unsaturated monoolefinic aliphatic hydrocarbon. Preferred vinyl-olefins are those containing at least 4 and up to 20 or more carbon atoms. The process is more valuable with olefin which contain 6 or more carbon atoms and especially eight or more carbon atoms, e.g. 6–30 carbon atoms, and most preferably at least 8 carbon atoms, e.g. 1-octene, 1-decene, 1-dodecene, 1-tetradecene, 1-hexadecene, 1-octadecene, 1-eicosene and the like including mixtures thereof.

Any trialkyl aluminum may be used as a catalyst in the process. Dialkyl aluminum hydrides may also be used and are considered equivalent and in fact may react in the reaction mixture to form aluminum trialkyls.

The preferred aluminum alkyls are the tri-$C_{1-12}$ alkyl aluminums such as trimethyl aluminum, triethyl aluminum, tri-butyl aluminum, tri-octyl aluminum, tri-decyl aluminum, tri-dodecyl aluminum and the like including mixtures thereof.

The more preferred aluminum alkyls are the higher aluminum alkyls such as the tri-$C_{4-10}$ alkyl aluminum. Most preferably the alkyls bonded to aluminum have the same or close to the same number of carbon atoms as the vinyl-olefin starting material. For example tri-n-octyl aluminum is the most preferred catalyst for dimerizing 1-octene.

The amount of aluminum alkyl catalyst is quite low. It will be shown later that this feature is critical because higher amounts of aluminum alkyls result in the formation of unacceptable quantities of internal olefins, both monomeric and dimeric.

A preferred catalyst concentration is 0.001–0.04 moles of aluminum alkyl per mole of initial vinyl-olefin. A more preferred concentration is about 0.01–0.04 moles of aluminum alkyl per mole of initial vinyl-olefin. A still more preferred concentration is 0.01–0.03 moles per mole of initial vinyl olefin. Excellent results have been achieved using about 0.015–0.02 moles of aluminum alkyl per mole of initial vinyl-olefin.

Since the amount of aluminum alkyl catalyst is so low, it is important that the initial vinyl olefin be essentially dry so that the catalyst is not deactivated by the water in the vinyl-olefin. If it is known that some water is present in the vinyl-olefin by means such as Karl Fischer water analysis, the amount of aluminum alkyl catalyst can be increased to compensate for the water or other active hydrogen component such as alcohol such that the amount of active aluminum alkyl catalyst remains in the critical range even after part of the initial aluminum alkyl has been destroyed by the water or other active hydrogen compound. Alternatively, the olefin feed can be pretreated to remove water or alcohol contamination. Likewise the process should be conducted under an inert atmosphere to prevent catalyst destruction.

The reaction temperature has been found to be another critical factor. This will be shown in the later examples. A preferred temperature range is about 100°–140° C. At 172° C. the process leads to excessive internal olefins both monomer and dimer even when the preferred low concentration of aluminum alkyl catalyst is used.

A more preferred process temperature is about 110°–130° C. Excellent results have been achieved at about 120° C.

The reaction rate under the conditions of the invention is quite slow so a long reaction time is required. The reaction should be conducted for a time sufficient to convert a substantial amount of initial vinyl-olefin to some other product, mainly vinylidene olefin dimer. Preferably the reaction is conducted for a time sufficient to convert at least 80 mole percent of the initial vinyl-olefin. More preferably the process is conducted long enough to convert at least 90 mole percent of the initial vinyl-olefin to some other component.

The time required for 90 percent conversion at 120° C. ranges from about 94 hours using 0.043 moles of aluminum alkyl catalyst per mole of initial vinyl-olefin up to 192 hours when using 0.017 moles per mole of initial vinyl-olefins. This information is to assist in planning initial experiments and is not intended as a limitation on the invention.

Several experiments were conducted to show how the process is conducted and to compare the results achieved within the critical claim limitations to those obtained outside the critical claim limitations. The experiments were conducted by placing the indicated amount of the trialkyl aluminum catalyst in the dried vinyl-olefin starting material and stirring the solution under dry nitrogen for the time indicated. Samples were withdrawn as the reaction proceeded and analyzed by gas chromatography (GC) and NMR to determine percent conversion and product composition.

EXAMPLES 1–5

This series of five experiments was conducted at 120° C. using various concentrations of tri-n-octyl aluminum (TNOA) catalyst. Examples 1–4 were carried out with 1-decene and Example 5 with 1-octene. The reaction period for each experiment was that required to convert 90 percent of the starting 1-octene or 1-decene to a different compound. Catalyst concentration is in terms of moles TNOA per mole initial 1-octene or 1-decene.

| Example | TNOA Conc. | Hrs. to 90% Conv. | Percent Selectivity (wt %) of Converted 1-Octene or 1-Decene | | |
|---|---|---|---|---|---|
| | | | β-internal Monomer | Deep Int. Dimer | Vinylidene Dimer |
| 1 | 0.67 | 26 | 13 | 17 | 70 |
| 2 | 0.33 | 28 | 11 | 8 | 81 |
| 3 | 0.17 | 35 | 7 | 8 | 85 |
| 4 | 0.043 | 94 | 4 | 6 | 90 |
| 5 | 0.017 | 192 | 1 | 4 | 95 |

These results show that at 120° C. the selectivity of converted vinyl-olefin to form vinylidene dimer increase sharply as the catalyst concentration decreases below 0.043 moles per mole of α-olefin and especially high, viz. 90 percent and 95 percent, as the catalyst concentration decreases to 0.017 moles per mole vinyl-olefin.

EXAMPLE 6

This experiment was conducted with 1-decene using TNOA catalyst at a concentration of 0.043 moles per mole 1-decene as in Example 4 and at a temperature of 172° C. which is outside the present invention. The process was conducted until 90 percent conversion of 1-decene was obtained. The results compared to Example 4 are given in the following table.

| Example | TNOA Conc. | Hrs. to 90% Conv. | Percent Selectivity (wt %) of Converted 1-Decene | | |
|---|---|---|---|---|---|
| | | | β-internal Monomer | Deep Int. Dimer | Vinylidene Dimer |
| 4 | 0.043 | 94 | 4 | 6 | 90 |
| 6 | 0.043 | 5 | 15 | 14 | 71 |

These results show that although the reaction is faster at 172° C. compared to 120° C., the selectivity to vinylidene dimer is only 71 percent compared to 90 percent with the same catalyst concentration but at 120° C.

A series of five experiments was carried out to show the progress of vinyl-olefin conversion over a period of time and the amount of β-internal olefin monomer formed during the course of the reaction. The catalyst in these experiments was TNOA and the olefin was 1-decene or 1-octene. The reaction temperature was 120° C. in all five experiments. The amount of TNOA catalyst was sequentially decreased from a TNOA/vinyl olefin mole ratio of 0.67 down to 0.017 over the five experiments. The results of the five experiments are given in the following table.

EXAMPLE 7–11

| React. Time (hrs) | Catalyst/Olefin Mole Ratio | | | | | | | | | |
|---|---|---|---|---|---|---|---|---|---|---|
| | 0.67[3] | | 0.33[3] | | 0.17[3] | | 0.043[3] | | 0.017[4] | |
| | Conv[1] | β-Int[2] | Conv[2] | β-Int | Conv | β-Int | Conv | β-Int | Conv | β-Int |
| 3 | 28.7 | 12.9 | 21.7 | 12.2 | 20.4 | 4.8 | — | — | — | — |
| 4 | 39.2 | 12.0 | 24.9 | 12.2 | 25.0 | 5.1 | — | — | — | — |
| 5 | — | — | 32.8 | 10.6 | — | — | — | — | — | — |
| 6 | 52.4 | 11.7 | — | — | 33.0 | 6.0 | — | — | — | — |
| 7 | — | — | 43.5 | 10.7 | — | — | — | — | — | — |
| 9 | — | — | 53.9 | 9.9 | — | — | — | — | — | — |

-continued

| React. Time (hrs) | Catalyst/Olefin Mole Ratio | | | | | | | | | |
|---|---|---|---|---|---|---|---|---|---|---|
| | 0.67[3] | | 0.33[3] | | 0.17[3] | | 0.043[3] | | 0.017[4] | |
| | Conv[1] | β-Int[2] | Conv[2] | β-Int | Conv | β-Int | Conv | β-Int | Conv | β-Int |
| 23 | 86.0 | 13.3 | 84.2 | 10.6 | 77.4 | 6.8 | — | — | — | — |
| 24 | — | — | — | — | — | — | 47.1 | 3.8 | — | — |
| 29 | 89.1 | 12.5 | — | — | 85.2 | 6.7 | — | — | — | — |
| 40 | — | — | — | — | — | — | — | — | 36.5 | 1.7 |
| 46 | — | — | — | — | 92.5 | 6.9 | — | — | — | — |
| 64 | — | — | — | — | — | — | — | — | 53.4 | 1.4 |
| 70 | — | — | — | — | — | — | 88.3 | 3.2 | — | — |
| 96 | — | — | — | — | — | — | 92.4 | 3.9 | — | — |
| 136 | — | — | — | — | — | — | — | — | 82.3 | 1.1 |
| 160 | — | — | — | — | — | — | — | — | 85.0 | 1.3 |
| 184 | — | — | — | — | — | — | — | — | 89.0 | 1.2 |

[1] Percent total conversion of initial vinyl olefin.
[2] Percent of converted vinyl olefin that formed β-internal olefin, i.e. β-internal olefin selectivity. The dimer selectivity (vinylidene & deep internal) is equal to 1-β internal selectivity.
[3] Conducted with 1-decene.
[4] Conducted with 1-octene.

The test results show that as the conversion of the vinyl-olefin (i.e. 1-decene or 1-octene) proceeds up to about 90 percent, the weight percent of β-internal olefin monomers relative to the converted 1-octene remains substantially constant at all catalyst levels. However at the lower concentrations, e.g. 0.043 and 0.017 moles TNOA/mole initial 1-decene or 1-octene, the percent selectivity to β-internal olefin monomers was extremely low and remained constant during the entire reaction.

Ziegler U.S. Pat. No. 2,695,327 suggests that internal di-substituted olefins undergo isomerization and are finally converted to vinylidene dimers. Under the low temperature, low catalyst concentration of the present invention it was found that internal monomeric olefins, e.g. octene-2, did not form any substantial amount of vinylidene dimers but formed mainly deep internal (non-vinylidene) dimers. This is shown in the following example.

EXAMPLE 12

In this example dry octene-2 containing 0.17 moles TNOA per mole octene-2 was stirred under nitrogen at 120° C. Samples were periodically withdrawn and analyzed by GC and NMR giving the following results.

| Time (hrs) | Composition (mole %) | | | | |
|---|---|---|---|---|---|
| | Vinyl | β-Internal | Deep Internal | Vinylidene Dimers | tri-Subst. |
| 0 | 0 | 93.1 | 6.9 | 0 | 0 |
| 0.5 | 0 | 92.0 | 8.0 | 0 | 0 |
| 3.0 | 0 | 89.2 | 9.9 | 0.9 | 0 |
| 5.0 | 0 | 83.3 | 15.9 | 0.8 | 0 |
| 7.0 | 0 | 79.5 | 19.8 | 0.7 | 0 |
| 24.0 | 0 | 57.1 | 41.6 | 1.3 | 0 |
| 47.0 | 0 | 46.2 | 51.5 | 2.3 | 0 |
| 47.5 | 0 | 45.7 | 52.8 | 1.6 | 0 |
| 72.0 | 0 | 38.9 | 59.0 | 2.1 | 0 |
| 96.0 | 0.4 | 31.4 | 56.2 | 3.2 | 8.8 |

The results of this example show that even after 96 hours an internal olefin monomer, viz octene-2, formed only about 3 mole percent vinylidene dimer. The main products were deep internal $C_{16}$ dimers.

EXAMPLE 13

This example was conducted in the same manner as Example 12 (120° C., 0.17 moles TNOA/mole 1-decene) except a vinyl-olefin, viz decene-1, was used. The results are given in the following table.

| Time (hrs) | Composition (mole %) | | | | |
|---|---|---|---|---|---|
| | Vinyl Monomer | Internal Monomer | Internal Dimer | Vinylidene Dimers | Tri-Substituted Dimer |
| 0 | 95.0 | 1.1 | 0.3 | 3.6 | 0 |
| 0.5 | 93.8 | 1.2 | 0.7 | 4.4 | 0 |
| 1.0 | 92.5 | 1.3 | 0.7 | 5.5 | 0 |
| 1.5 | 91.0 | 1.3 | 1.0 | 6.7 | 0 |
| 2.0 | 89.2 | 1.7 | 0.7 | 8.4 | 0 |
| 3.0 | 85.6 | 2.0 | 1.1 | 11.3 | 0 |
| 4.0 | 82.2 | 2.2 | 1.6 | 14.0 | 0 |
| 6.0 | 74.6 | 3.2 | 2.1 | 20.1 | 0 |
| 23.0 | 31.5 | 8.6 | 4.6 | 55.3 | 0 |
| 29.0 | 21.6 | 10.0 | 5.9 | 62.5 | 0 |
| 46.0 | 11.2 | 12.1 | 6.3 | 70.4 | 0 |

The results show that as the vinyl-olefin is converted, the major product formed is vinylidene dimer. However a substantial amount of internal monomer (i.e. β-internal) also forms as well as internal olefin dimer (i.e. di-substituted olefin). It is significant that the quantity of internal olefin monomer continues to slowly increase as the reaction proceeds which indicates it is not being isomerized back to vinyl-olefin and converted to vinylidene dimer.

EXAMPLE 14-15

These two examples show the progress of the present invention when conducted at 120° C. using low TNOA catalyst levels (Example 14—0.043 moles, Example 15—0.017 moles). The vinyl-olefin starting material was 1-decene in Example 14 and 1-octene in Example 15. The following table shows the progress of the reaction.

| Time (Hrs) | Composition (Mole %) | | | | | | | |
|---|---|---|---|---|---|---|---|---|
| | Vinyl Monomer | | β-Internal Monomer | | Deep Internal Dimer | | Vinylidene Dimer | |
| | Ex 14 | Ex 15 | Ex 14 | Ex 15 | Ex 14 | Ex 15 | Ex 14 | Ex 15 |
| 0 | 95.5 | 97.2 | 0.7 | 0.4 | 0.7 | 0.4 | 3.1 | 2.0 |

-continued

| Time (Hrs) | Vinyl Monomer | | β-Internal Monomer | | Deep Internal Dimer | | Vinylidene Dimer | |
|---|---|---|---|---|---|---|---|---|
| | Ex 14 | Ex 15 | Ex 14 | Ex 15 | Ex 14 | Ex 15 | Ex 14 | Ex 15 |
| 3 | 91.6 | — | 0.7 | — | 0.7 | — | 7.0 | — |
| 5 | 89.6 | — | 0.7 | — | 0.7 | — | 9.0 | — |
| 7 | 85.5 | — | 1.1 | — | 1.1 | — | 12.2 | — |
| 16 | — | 88.5 | — | 0.9 | — | 0.5 | — | 10.1 |
| 24 | 60.6 | — | 2.9 | — | 2.1 | — | 34.4 | — |
| 40 | — | 73.4 | — | 1.1 | — | 1.3 | — | 24.1 |
| 47 | 33.8 | — | 4.6 | — | 3.6 | — | 58.0 | — |
| 64 | — | 59.5 | — | 1.5 | — | 1.6 | — | 37.3 |
| 70 | 17.4 | — | 5.5 | — | 4.8 | — | 72.3 | — |
| 96 | 10.9 | — | 5.8 | — | 5.8 | — | 76.9 | — |
| 136 | — | 25.9 | — | 2.4 | — | 2.8 | — | 68.9 |
| 160 | — | 21.3 | — | 2.4 | — | 3.7 | — | 72.6 |
| 184 | — | 16.5 | — | 2.7 | — | 3.8 | — | 77.1 |

The results show that at 120° C. at both low catalyst concentrations the major products are the vinylidene dimers and only small amounts of β-internal monomer or deep internal dimer appear in the product. The 76.9 mole percent vinylidene dimer in Example 14 after 96 hours and 77.1 mole percent vinylidene dimer in Example 15 after 184 hours represent selectivities to vinylidene dimers of 91.3 weight percent and 94.8 weight percent respectively after correcting for unconverted vinyl-olefin both at the start of the run and at the end of the run.

We claim:

1. A process for dimerizing a vinyl-olefin monomer at a selectivity of at least 85 mole percent to form vinylidene olefins, said process comprises dimerizing a vinyl-olefin containing 4 to about 30 carbon atoms in the presence of a catalyst, which catalyst consists essentially of 0.001-0.04 moles of tri-alkyl aluminum per mole of said vinyl-olefin, at a temperature in the range of about 100°-140° C. for a time sufficient to convert at least 80 mole percent of the initial vinyl-olefin to a different product.

2. A process of claim 1 wherein said catalyst consists essentially of about 0.01-0.04 moles of tri-alkyl aluminum per mole of said vinyl-olefin.

3. A process of claim 2 wherein said temperature is 110°-130° C.

4. A process of claim 3 wherein said tri-alkyl aluminum is a tri-$C_{4-10}$ alkyl aluminum.

5. A process of claim 4 wherein said tri-$C_{4-10}$ alkyl aluminum is tri-n-octyl aluminum.

6. A process of claim 1 wherein said vinyl-olefin contains about 6–30 carbon atoms.

7. A process of claim 6 wherein said catalyst concentration is about 0.01–0.03 moles per mole of said α-olefin.

8. A process of claim 7 wherein said temperature is 110°-130° C.

9. A process of claim 8 wherein said tri-alkyl aluminum is a tri-$C_{4-10}$ alkyl aluminum.

10. A process of claim 9 wherein said tri-$C_{4-10}$ alkyl aluminum is tri-n-octyl aluminum.

11. A process of claim 1 conducted for a time sufficient to convert at least 90 mole percent of the initial vinyl olefin to a different product.

12. A process for dimerizing 1-octene to form a reaction product that, excluding unconverted 1-octene, comprises 90–95 weight percent $C_{16}$ vinylidene olefin, said process comprising forming a mixture of 1 mole part of dry 1-octene and 0.001–0.04 mole parts of tri-n-octyl aluminum and reacting said mixture in a substantially inert environment at a temperature in the range of 110°-130° C. for a time sufficient to convert at least 90 weight percent of the initial 1-octene to a different product.

13. A process of claim 12 conducted at about 120° C. in the presence of about 0.01–0.03 mole parts of tri-n-octyl per mole part of initial 1-octene.

14. A process for dimerizing 1-decene to form a reaction product that, excluding unconverted 1-decene, comprises 90–95 weight percent $C_{20}$ vinylidene olefin, said process comprising forming a mixture of 1 mole part of dry 1-decene and 0.001–0.04 mole parts of tri-n-octyl aluminum or tri-n-decyl aluminum or mixtures thereof and reacting said mixture in a substantially inert environment at a temperature in the range of 110°-130° C. for a time sufficient to convert at least 90 weight percent of the initial 1-decene to a different product.

15. A process of claim 14 conducted at about 120° C. in the presence of about 0.01–0.03 mole parts of tri-n-octyl aluminum or tri-n-decyl aluminum or mixtures thereof per mole part of initial 1-decene.

16. A process for dimerizing a vinyl-olefin monomer at a selectivity of at least 85 mole percent to form vinylidene olefins, said process comprises dimerizing a vinyl-olefin containing at least 8 carbon atoms in the presence of 0.001–0.04 moles of tri-alkyl aluminum catalyst per mole of said vinyl-olefin, at a temperature in the range of about 100°-140° C. for a time sufficient to convert at least 80 percent of the initial vinyl-olefin to a different product.

* * * * *

UNITED STATES PATENT AND TRADEMARK OFFICE
CERTIFICATE OF CORRECTION

PATENT NO. : 4,973,788
DATED : NOVEMBER 27, 1990
INVENTOR(S) : KAUNG-FAR LIN, ET AL.

It is certified that error appears in the above-identified patent and that said Letters Patent is hereby corrected as shown below:

Column 8, line 58, reads "80 percent" and should read
-- 80 mole percent --.

Signed and Sealed this

Seventeenth Day of November, 1992

Attest:

DOUGLAS B. COMER

*Attesting Officer*  *Acting Commissioner of Patents and Trademarks*